United States Patent [19]

Sonsteby

[11] Patent Number: 4,865,549
[45] Date of Patent: Sep. 12, 1989

[54] MEDICAL DOCUMENTATION AND ASSESSMENT APPARATUS

[75] Inventor: Kristi L. Sonsteby, Dallas, Tex.

[73] Assignee: Kristicare, Inc., Austin, Tex.

[21] Appl. No.: 181,544

[22] Filed: Apr. 14, 1988

[51] Int. Cl.⁴ ............................ G09F 3/00; A61B 5/00
[52] U.S. Cl. ...................................... 434/262; 40/359; 40/360; 128/771
[58] Field of Search ...................... 434/262, 178, 433; 40/359, 360; 283/101; 128/630, 771

[56] References Cited

U.S. PATENT DOCUMENTS 3,698,383 10/1972 Baucom .............................. 128/771
3,818,897 6/1974 Smith .................................. 128/771
3,962,807 6/1976 Pantone ................................ 40/359

FOREIGN PATENT DOCUMENTS 502195 of 1939 United Kingdom ................ 434/178

*Primary Examiner*—Edward M. Coven
*Assistant Examiner*—Valerie Szczepanik
*Attorney, Agent, or Firm*—Ross, Howison, Clapp & Korn

[57] ABSTRACT

A documentation system that allows adequate control of documentation in addition to an assessment of skills of the professionals involved includes a plurality of sections, each section dedicated to a particular body system. Each of the sections has disposed therein a plurality of peel-off labels, each label providing a series of assessment steps. Each of the labels has a distinctive color associated with the particular section that it is disposed in, with the text also being in the associated distinctive color. A diagnostic label is also provided which has the title thereof in the distinctive color with the type thereof being in black and white. The labels are operable to be removed and temporarily placed on the chart of the patient during an acute episode, incident or accident.

10 Claims, 1 Drawing Sheet

MEDICAL DOCUMENTATION AND ASSESSMENT APPARATUS

TECHNICAL FIELD OF THE INVENTION

The present invention pertains in general to documentation systems, and more particularly, to a documentation system that allows adequate control of documentation involved in the health care industry in addition to an assessment of skills of the professionals involved.

BACKGROUND OF THE INVENTION

Documentation systems in the health care field have seen increased demand due to the increasing liability in that industry. The need for documentation systems is especially acute in present day health care systems to insure that well-run institutions remain in business. This is especially true when considering the fact that larger and larger numbers of individuals are being processed by the health care systems. It is this increased number of patients that provides the increased demand for documentation.

One type of problem that occurs in the documentation procedure of present day health care institutions is that involved with the nurse/patient relationship. When a patient is entered into the hospital, it is necessary to quickly identify the patient's condition and flag this condition for the nursing staff especially when an acute episode or accident is involved that requires specific follow-up care. Typically, the nursing staff runs in shifts with each shift having to deal with a relatively large number of patients. To insure that there is a continuity between two shifts, it is important that each nurse entering a new shift has properly recorded all information concerning each of the patients. Typically, the only information that the nurse has on this patient is the chart. In order to adequately access a problem with the patient to determine what action to take and how often, the nurse must be able to quickly review the chart to determine the complete status of the patient and then make a determination as to what the problem is. Further, the nurse must document everything that has been done during this decision-making process. This can present a problem to any health care professional in that the appropriate medical terminology, etc., is not always fresh in their mind. This is especially true when handling a number of different anatomical systems such as the cardiovascular system, the genitourinary system, etc. To insure more complete documentation, it is desirable to provide a system whereby the health care professional can have ready access to the specific procedures that must be performed under any situation and clearly and succinctly document these procedures with the appropriate medical terminology.

SUMMARY OF THE INVENTION

The present invention disclosed and claimed herein comprises a documentation system for the medical field. The documentation system contains a plurality of information sections with each of the sections containing predetermined assessment information associated with a separate and particular body system. Each of the sections has a particular color associated therewith and each of the sections includes a divider and a plurality of information packets. The divider defines the associated sections apart from the others to allow selection thereof. Selection is available as a function of the associated color. Medical reference terminology and anatomical diagrams are provided on the divider and limited to the predetermined assessment information associated with that section. A plurality of modularized information packets each containing a plurality of predetermined assessment steps are defined in text. The text is formed in the color of the associated section. Each of the information packets is removed when required for an acute episode or follow-up procedure and attached to a patient's chart when the information on the modularized packets is utilized by the medical professional in accessing a patient's condition. After the follow-up procedure is complete, the modularized packet is removed from the patient's chart.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
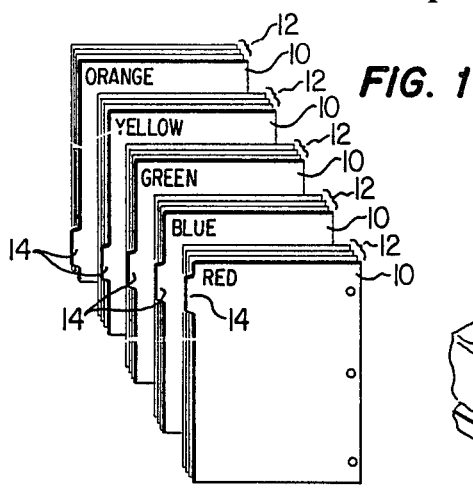
FIG. 1 illustrates a perspective blow-up of the documentation system of the present invention.

Referring now to FIG. 1 there is illustrated a perspective blow-up of the documentation system of the present invention. The documentation system is comprised of a plurality of color-coded sections, each identified by a separate divider 10. Each divider 10, in the illustrated embodiment, is defined as having the colors red, blue, green, yellow and orange. Each section corresponds with a different body system, such as urinary or cardiovascular, and includes all of the information necessary for a thorough assessment. In the preferred embodiment, there are twelve color-coded sections, although only five sections are illustrated. The sections are as follows:

Cardiovascular
Gastrointestinal
Genital/Urinary Area
Head, Ears, Eyes, Nose, Throat
Hematopoietic, Integumentary
Metabolic/Endocrine
Musculoskeletal
Neurological
Psychological
Pulmonary
Reproductive Each section has contained therein a plurality of sheets of assessment and/or diagnostic labels on sheets 12. In use, the health care professional need only access the appropriate color-coded section by selecting the section on a tab 14 on each of the dividers 10 to determine which label is to be associated with a particular patient. For example, if a patient has entered into the hospital for a cardiovascular problem, the cardiovascular divider 10 is selected and the appropriate label removed from the associated one of sheets 12 and attached to the patient's chart. This assessment and/or diagnostic label is then utilized to aid the health care professional in the subsequent diagnostic procedures.

Figure 2:
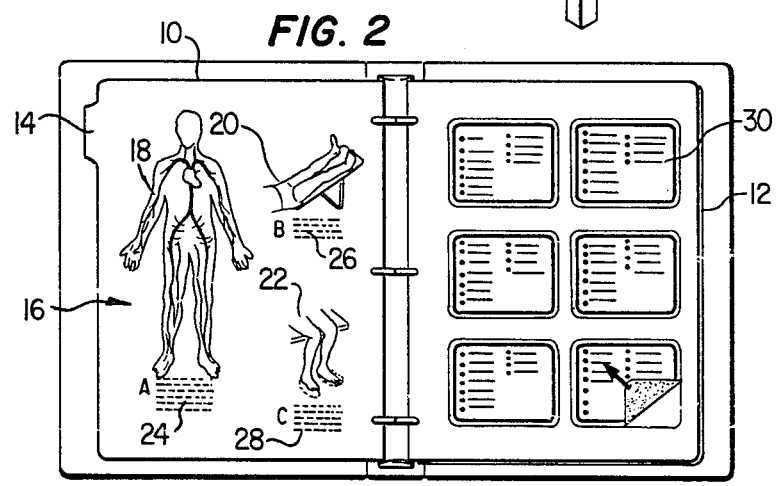
FIG. 2 illustrates one section of the documentation system illustrating the pull-off labels.

Referring now to FIG. 2, there is illustrated a detail of one of the sections illustrating the inside of the divider 10 and one of the sheets 12 associated therewith. The inside of the sheet 10 has an associated medical diagram disposed thereon which is referred to as an assessment alert 16. This contains an anatomical diagram and associated medical terminology. This assessment alert illustrates the proper anatomy and physiology terms and acts generally as a reminder. For example, the section illustrated in FIG. 2 is associated with the cardiovascular system. With respect to this body system, there are three diagrams provided in the assessment alert 16. These are diagrams 18, 20 and 22. Diagram 18 is associated with text 24 labelled A, diagram 20 is associated with text 26 labelled B, and diagram 22 is associated with text 28 labelled C. The diagram 18 contains the anatomical structure of the cardiovascular system and the appropriate medical labels and terminology. For example, the diagram would contain and define the carotid artery, subclavian artery, brachial artery, abdominal aorta, etc. The text associated therewith would provide the general evaluation tools in assessing the general condition of a patient associated with a cardiovascular problem. In the preferred embodiment, the text 24 illustrated in Table 1:

TABLE I

A. Evaluate

1. Amplitude of pulsation
2. Quality of pulsation
3. Presence of abdominal bruit
(particularly in carotid, subclavian,
abdominal aorta and femoral arteries)
4. Color and temperature of skin
5. Postural changes (See B and C)

The diagram 20 associated with the text 26 labelled B is a diagram showing the various elevations associated with postural changes whereas the diagram 22 is associated with dependency and illustrates the various techniques associated with dependency, such as allowing the feet to hang over the side of the bed in order to note the time that it takes for normal color to return. The text 28 associated therewith provides the tools assessing dependency and is illustrated in Table 2 and the text 28 illustrates in Table 3.

TABLE 2

B. Elevation:

1. Elevate extremities for 30–60 seconds.
2. Note degree and location of color changes.

TABLE 3

C. Dependency:

1. After noting responses to elevation, allow feet to hang over side of bed and note the time it takes for normal color to return.
2. Normal - 10 seconds 35–45 seconds suggests marked impairment.
3. Dependent rubor may develop if schemia is TABLE 3-continued C. Dependency:

severe.

The divider 10 on the inside cover thereof therefore illustrates salient points in evaluating peripheral arterial insufficiency with respect to the cardiovascular system. In a similar manner, each of the dividers 10 would provide on the inside covers thereof a very succinct set of reminders for making an initial assessment. For example, in the genital/urinary section, the assessment alert diagram 16 would provide a nursing assessment for urinary retention. To attain this assessment, there is a particular procedure which should be followed in most situations. This is outlined with the general medical terminology to first of all insure that the procedure has been carried out and second to provide the nurse with a guideline for documenting this procedure on the patient's chart.

Figure 3:
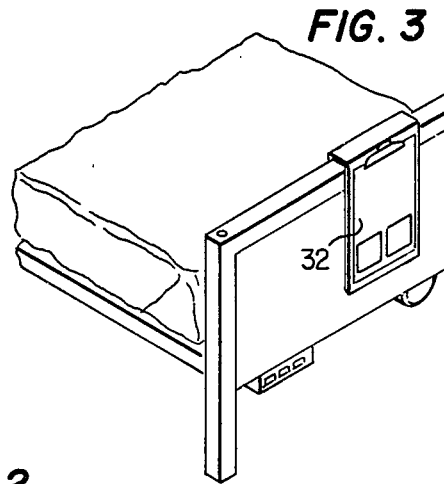
FIG. 3 illustrates the attachment method for the labels.

The peel-off label sheets 12 are comprised of a plurality of identical labels of 30 of which there are six in the preferred embodiment. Each of the labels 30 is color-coded identical to the divider 10 in accordance with the associated body system and contains concise information. This concise information provides assessment body information for assessing change of condition, acute episode, incident or accident. In addition, the information provides for a routine diagnosis, treatment, special conditions, admissions or discharge. As will be described hereinbelow, the color-coding also determines whether the label is provided merely for assessment or for diagnosis, there being a distinction between the two. Each of the labels 30 is operable to be peeled off and attached to the patient's chart. This is illustrated in FIG. 3 wherein a chart 32 is associated with each patient and normally it is disposed either at the nursing station in a rack or at the patient's bedside. Typically, these charts are disposed at the nursing station and can be accessed any time a member of the professional staff is going to visit the patient for the purposes of accessing his condition and/or treatment.

In operation of the documentation system, the patient is initially assessed as to a complaint for a particular body system such as cardiovascular, genital/urinary, etc. The appropriate body system is then identified for the appropriate follow-up. The associated label 30 is then peeled off the sheet 12 and placed on the front of the patient's chart 32. More than one label can be disposed thereon depending upon the various body systems that need follow-up. The chart is then placed in the appropriate area, such as near the patient or in a particular rack. The medical professional's notes are then documented each shift for follow-up on acute episode, incident accident or change of condition. Typically, this is done on a minimum period of 48–72 hours. When the episode is resolved, or follow-up is no longer necessary, the label is then peeled off. Therefore, the label with its distinctive color-coding indicates that follow-up and documentation is necessary to insure that this action is done, in addition to providing the salient information thereon. Once the label is removed, the chart can be placed back in an appropriate place for normal care in the particular medical facility.

Figures 4, 5:
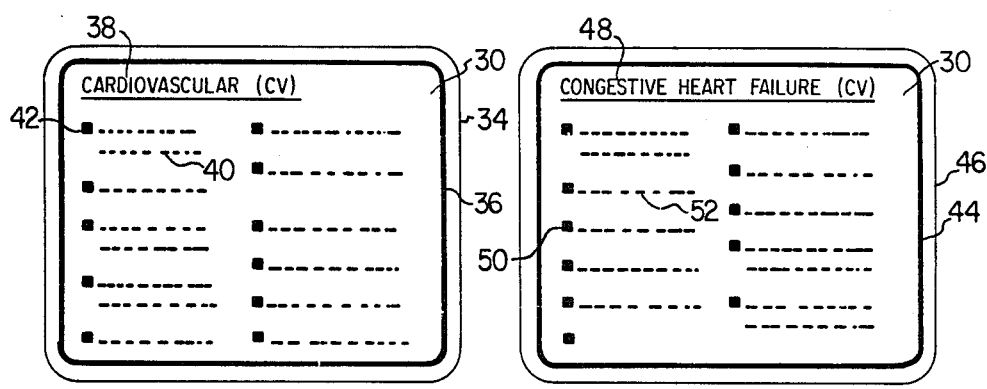
FIG. 4 illustrates one of the assessment labels associated with the assessment portion of the present invention.
FIG. 5 illustrates a label illustrating the diagnostic and information portion of the present documentation system.

Referring now to FIG. 4, there is illustrated a detail of one of the labels 30 affixed to the sheet 12. The label 30 is defined by a boundary 34 which represents a cut or separation between the label 30 and the remainder of the sheet 12. This is provided by conventional processing whereby a sheet of paper having an adhesive backing is attached to a second sheet having a waxlike surface. Cuts are then impressed on the sheet of paper which only penetrate to the depth of the top sheet. This provides the boundary 34 such that at a later time the label 30 can be peeled off leaving the remainder of the sheet.

A colored border 36 surrounds the label 30 and inside border 36, the colored border 36 being of the color of the associated body system and divider 10. Each of the labels 30 has associated therewith a heading 38 that is comprised of bold letters in the color of the associated body system and a plurality of short phrases 40 in textual format, each phrase having a "bullet" 42 associated therewith at the beginning. Each of the bullets essentially represents the beginning of a particular task or assessment tool. For the label 30 illustrated in FIG. 4, the title 38 is illustrated as being "Cardiovascular (CV)" which represents the general assessment label for the Cardiovascular divider 10. This represents the general assessment provided for the cardiovascular system. For the assessment label 30, the bullets 42 are red and the text 40 is red such that the print on the entire label is therefore red. This color indicates what must be gone through on a checklist format in order to provide an accurate assessment for change of condition, acute episode, incident or accident. The completely colored label 30 wherein all of the text 40, headings 38 and bullets 42 are colored indicates that this is an assessment label. The text of the assessment label 30 for the cardiovascular system illustrated in FIG. 4 is defined in Table 4:

TABLE 4

| Cardiovascular (CV) |
| --- |
| Complete vital signs |
| Pain (location) |
| Strength and regularity of pulse |
| Apical-Radial deficit |
| Edema-peripheral and sacral edema (1+–4+) |
| Quality of bilateral peripheral pulses |
| Homan's sign |
| Skin, warm and dry |
| Significant changes in blood pressure |
| Palpitations |
| Neck vein distension |
| Color (skin, nails, lips) |
| Shortness of breath |
| Bovine graft or A-V fistula |

Referring now to FIG. 5, there is illustrated one of the labels 30 associated with the diagnostic and information aspect of the present invention. This would not be in the same category as the assessment, but would be a subcategory. The assessment label 30 has a colored border 44 disposed therearound with the boundaries the color of the diagnostic label 30 being represented by a border 46. The border 44 is the color of the associated body system. The diagnostic label 30 also has a heading 48, bullets 50 and text 52, similar to the heading 38, bullets 42 and text 40 of the label 30 of FIG. 4. However, the text 52 in black and white to indicate that this is a diagnostic label. The diagnostic label is only disposed on the patient's chart after the acute episode is resolved or follow-up is no longer necessary. In the diagnostic label 30 illustrated in FIG. 5, the heading 48 is associated with congestive heart failure (V) which is associated with the cardiovascular body system Therefore, it would be disposed in the same divider 10 as the assessment label 30 of FIG. 4, but would be provided merely for diagnostic purposes The text found in the diagnostic label 30 is defined in Table 5:

TABLE 5

| Congestive Heart Failure (CV) |
| --- |
| Complete vital signs (apical heart rate) |
| Weight (daily) |
| Dyspnea |
| Diet (sodium-restricted), (renal function) |
| Diuretics (type), (dosage), (electrolyte depletion) |
| I & O |
| Weakness (malaise), (fatigue) |
| Sleep Patterns |
| Edema (1+–4+) every shift |
| Anxiety - Oxygen (rate) (how often) |
| Mobility (ambulation status) |
| Lung sounds (describe) |
| Color |
| Sputum (color), (amount) |
| HOB elevated (how many degrees) |

After the label 30 has been placed on the patient's chart, a nurse coming on a shift can very quickly determine if the chart is associated with an episode or follow-up by first determining whether the chart is in an appropriate rack and second, determining the color-coding on the label to determine of it is an acute episode or primarily routine care. Once this is determined, the nurse is provided a succinct checklist each time the patient is checked on. Therefore, it can be insured that the nurse has performed her job thoroughly since this checklist also provides the nurse with the appropriate medical terminology to enter into their notes. If the nurse requires any further information, the diagram 16 on the color-coded divider 10 can be received to give the nurse some additional background. Prior to the present documentation system, a nurse was required to refer to a textbook or other notes, etc. that had been provided for this type of procedure. With the documentation system of the present invention, everything is provided to the nurse or medical professional in a very succinct manner with the color-coding providing very clear distinctions as to what procedures should be performed. As described above, once the follow-up has been discontinued, the assessment label can be removed and the diagnostic label then placed thereon. This provides for additional follow-up and a more detailed checklist for this follow-up.

In summary, there has been provided a documentation system for the health care industry which includes a plurality of categorized dividers, each divider placed into a category associated with one of the body systems. Each of the dividers provides a section which is color-coded and has provided therein a plurality of identical labels. Each of the labels contains succinct assessment information and/or diagnostic information. This label is removable and operable to be adhered to a patient's chart. The label contains the color-coding of the associated section. Once placed onto the patient chart, the procedural tasks are outlined, which procedural tasks should be performed during any follow-up. The color-coding in addition to the particular information contained on the assessment label provides for a very succinct documentation and professional assessment tool.

Although the preferred embodiment has been described in detail, it should be understood that various changes, substitutions and alterations can be made therein without departing from the spirit and scope of the invention as defined by the appended claims.

What is claimed is:

1. A documentation apparatus for use in association with a patient's medical chart, comprising:
   a plurality of information sections, each of said sections containing predetermined assessment information associated with a separate and particular body system;
   each of said sections having a particular color associated therewith and each of said sections including:
      a divider sheet of paper for defining said associated section apart from the others of said sections to allow selection thereof according to color, said divider sheet of paper having a tab disposed thereon, said tab extending outward from the perimeter of said divider sheet of paper;
      medical reference terminology and anatomical diagrams limited to the predetermined assessment information associated with said section and said medical reference terminology, and said anatomical diagrams disposed on one side of said divider sheet of paper; and
      a plurality of modularized information packets associated with each of said sections each identical and each containing a plurality of predetermined assessment steps defined in text;
   said text being in the color of said associated section;
   said plurality of said information packets disposed on one of a plurality of packet sheets of paper, said packet sheets of paper operable to be disposed adjacent said divider sheet of paper with said information packets each comprised of a removable label that is adhered to one of said packet sheets of paper, said removable labels each dimensioned to fit on a patient's medical chart.

2. The documentation apparatus of claim 1 wherein each of said sections contains a predetermined title.

3. The documentation apparatus of claim 2 wherein each of said packets contains the title of said associated section in the color of said associated section.

4. The documentation apparatus of claim 1 wherein each of said labels on said packet means of paper has a colored border disposed on the peripheral edges thereof, said colored border being in the color of said associated section.

5. The documentation apparatus of claim 1 wherein each of said assessment steps comprises a predetermined textural description of said assessment step in the color of said associated section and each of said predetermined textural descriptions being preceded by an indicator marker, said indicator marker being in the color of said associated section.

6. The documentation apparatus of claim 1 and further comprising a diagnostic packet associated with each of said plurality of modularized information packets, said diagnostic packets comprising:
   a plurality of labels, each of said labels adhered to a sheet of paper;
   said diagnostic packets each containing a plurality of diagnostic steps with each diagnostic step comprising a textual diagnostic description;
   said textual diagnostic description being in a black and white format;
   each of said labels having a title in the color of said associated section and identical to the title of said associated section; and
   each of said diagnostic textual diagnostic descriptions preceded by an indicator mark being in the color of said associated section.

7. A medical documentation and skills assessment apparatus for use in association with a patient's medical chart, comprising a plurality of color-coded sections, each section associated with a separate and particular body system having a unique color associated therewith and each color-coded section including:
   a divider sheet having a color-coded tab in the color of said associated section disposed on the periphery thereof, said color-coded tab allowing selection of the associated section;
   reference terminology and diagrams associated with the body system of said associated section, said reference terminology and anatomical diagrams disposed on said divider sheets;
   a plurality of information sheets disposed adjacent said divider sheet and pertaining to said associated section; and
   a plurality of labels disposed on each of said information sheets and operable to be selectively removed therefrom and adhered to a patient's medical chart with each of said labels having an adhesive backing thereon;
   each of said labels having a heading identifying the body sections of the associated one of said sections and in the color of said associated section and textual assessment steps in the color of said associated section, each of said assessment steps defining an outline of the general assessment steps required for follow-up procedures on acute episode, accident or incident.

8. The documentation apparatus of claim 7 and further comprising a second set of labels disposed on select ones of said information sheets, each of said second sets of label having textual diagnostic information steps disposed thereon in black and white and operable to define diagnostic or procedural information.

9. A method for documenting care in a medical environment and in association with a patient's medical chart, comprising:
   defining a plurality of body systems;
   selecting one of the body systems;
   providing salient medical terminology and anatomical diagrams associated with each of the body systems for the purposes of assessing general conditions with respect to the associated body system;
   providing a plurality of removable assessment labels, each label dimensional to fit on a patient's medical chart;
   providing on each of the assessment labels a color-coded border in the color of the associated body system;
   providing on the label a plurality of assessment steps, each assessment step in a textual format in the color of the associated body system, each of the assessment steps providing predetermined assessment guidelines;
   providing on each of the labels a title of the associated body system;
   removing the label when follow-up for an acute episode, incident or accident is presented,
   attaching the removed label to a patient's chart for the duration of the follow-up procedure; and
   removing the label when the follow-up procedure is completed.

10. The method of claim 9 and further comprising:

providing a plurality of diagnostic information labels;
providing on each of the labels the title of the associated body system in the color of the associated body system;
providing a colored border around the peripheral edges of the label in the color of the associated body system;
providing textual diagnostic information steps in black and white containing pertinent diagnostic and informational steps pertinent to the associated body system;
removing the label; and
attaching the label to the chart of a patient for normal routine care.

* * * * *